United States Patent [19]

Woulfe et al.

[11] Patent Number: 5,112,595
[45] Date of Patent: May 12, 1992

[54] 99MTC(III) MYOCARDIAL IMAGING AGENTS AND METHOD OF USE

[75] Inventors: Steven R. Woulfe, Ballwin; Edward A. Deutsch, St. Louis; Mary M. Dyszlewski, Maryland Heights; William L. Neumann, Grover, all of Mo.

[73] Assignee: Mallinckrodt Medical, Inc., St. Louis, Mo.

[21] Appl. No.: 632,285

[22] Filed: Dec. 21, 1990

[51] Int. Cl.$^5$ .................... A61K 49/02; C07F 13/00
[52] U.S. Cl. ................................ 424/1.1; 534/14
[58] Field of Search ....................... 424/1.1; 534/14

[56] References Cited

U.S. PATENT DOCUMENTS

| | | | |
|---|---|---|---|
| 4,795,626 | 1/1989 | Deutsch et al. | 424/1.1 |
| 4,917,879 | 4/1990 | Deutsch et al. | 424/1.1 |
| 4,957,728 | 9/1990 | Deutsch et al. | 424/1.1 |

FOREIGN PATENT DOCUMENTS 0201005 11/1986 European Pat. Off. .

*Primary Examiner*—John S. Maples
*Attorney, Agent, or Firm*—David A. Hey

[57] ABSTRACT

A myocardial imaging agent for use in humans comprising a Tc(III) complex ligated in a planar position by a tetradentate ligand having incorporated therein four hard atoms and two furanone rings and in the axial positions by phosphines containing dioxanyl or ether moieties. The agent exhibits improved biodistribution, improved labeling and extremely rapid blood clearance following administration to a human. The agent has high myocardial uptake accompanied with exceptionally rapid hepatobilary clearance and extensive renal clearance to give sufficiently high heart/liver and heart/lung ratio that provide nearly ideal myocardial images in humans.

19 Claims, No Drawings

99MTC(III) MYOCARDIAL IMAGING AGENTS AND METHOD OF USE

BACKGROUND OF THE INVENTION

Several non-invasive methods of imaging body organs have been developed over the past decades. These methods are based on the tendency of particular body organs to concentrate particular chemicals which may be detectable. Particularly useful chemicals for these methods are those which emit gamma radiation. Subsequent scanning of the organ with a gamma ray camera provides an image of the organ from which diagnostic information can be obtained. $^{99m}$Tc (Tc-99m) has found particular utility in this area because of its half-life and gamma ray emission.

Over the past several years different Tc-99m compounds have been disclosed for use as positive myocardial imaging agents. These different imaging agents based on substantially different chemistries, have exhibited varying levels of utility in different mammals. To effectively image the heart, the agent must localize in the heart and at the same time rapidly clear from neighboring organs such as the lungs and in particular the liver. Further, the imaging agent must not bind tightly to the blood or else image quality will be poor. An imaging agent which localizes in the heart and at the same time localizes in the liver does not provide a good image of the heart since the apex of the human heart is often obscured by the liver.

Although detecting radiation from a radiation emitting pharmaceutical has proven particularly useful in non-invasive organ imaging, organ-specific radio-pharmaceuticals are still needed. For example, there is an especially strong need for an effective myocardial imaging agent. At the present time there are two known types of myocardial imaging agents. The positive agents which accumulate in an infarcted area of the heart and negative agents which accumulate in the normal healthy area of the heart but not in the infarcted areas. Using a positive agent causes an infarcted area to show up as a hot spot of radioactivity whereas with a negative agent the infarcted area shows up as a cold area against a hot background.

Over the past several years different Tc-99m compounds have been disclosed for use as positive myocardial imaging agents. These different imaging agents having substantially different chemistries have found various levels of utility in different mammals. To date it is still a goal of nuclear medicine to find a more effective negative myocardial imaging agent particularly suited for the human heart.

Work with myocardial imaging agents formed from Tc-99m was conducted by Deutsch, et al. as disclosed in U.S. Pat. No. 4,489,054. Deutsch, et al. determined that cationic lipophilic complexes of Tc-99m provide a useful myocardial image in mammals. This work provided particularly good images with certain mammals, particularly dogs. Technetium can assume several valence stages ranging from $+7$ to $-1$. The method disclosed in the Deutsch, et al. U.S. Pat. No. 4,489,054 disclosed technetium complexes in the $+3$ state. These subsequently were found to provide a relatively poor image of the human heart.

Further work conducted by Deutsch and Libson, et al. indicated that the complexes of Tc(I)-99m provided more useful heart images. These provided particularly good images of cat hearts. Unfortunately, with humans these images were obscured by accumulation of the technetium complex in the liver which interfered with obtaining a very good image of the heart. This information is disclosed in Deutsch, et al. U.S. Patent application Ser. No. 628,482 filed Jul. 6, 1984 incorporated in U.S. Pat. No. 4,795,626. Additional work disclosed in the Deutsch, et al. patent indicated that $^{99m}$Tc(I) compounds ligated to phosphonate and phosphonite ligands cleared the liver more quickly and provided an even better myocardial image than prior compounds. However, the $^{99m}$Tc(I) ligated compounds clear the liver exceptionally well, but do not clear from the blood to permit a useful image of the heart.

Other cationic ligated complexes of $^{99m}$Tc are disclosed, for example, in Rodriquez U.S. Pat. No. 4,497,790; Glavan, et al. U.S. Pat. No. 4,374,821; and Tweedle U.S. Pat. No. 4,455,291. Other technetium compounds are disclosed in European Patent Application 0123240.

SUMMARY OF THE INVENTION

The present invention is premised on the realization that Tc(III) myocardial imaging agents which are not reducible in vivo are very effective myocardial imaging agents. These Tc(III) myocardial agents are most effective when comprising a tetradentate ligand incorporating at least one furanone ring, four hard atoms, and capped with phosphines containing dioxanyl or ether moieties to provide technetium complexes in the $3+$ oxidation state.

More particularly, the present invention is premised on the realization that an effective myocardial imaging agent for humans can be prepared by ligating a tetradentate ligand system containing at least one furanone ring, although more preferably containing two furanone rings, to the four planar coordination bonding sites of an octahedrally coordinated technetium center and bonding phosphine ligands to the axial positions of the technetium center to provide a commercially viable heart imaging agent. Myocardial imaging agents so prepared exhibit substantially improved biodistribution and labeling properties. High myocardial uptake accompanied with exceptionally rapid hepatobilary clearance and extensive renal clearance gives sufficiently high heart/liver and heart/lung ratios to provide nearly ideal diagnostic myocardial images in humans.

DETAILED DESCRIPTION OF THE INVENTION

The technetium compounds of the present invention which have been found most useful as myocardial imaging agents in humans comprise hexadentate technetium complexes having an overall cationic charge. More specifically the agents comprise technetium complexes in the $3+$ oxidation state coordinatively bonded to six atoms as shown in Formula 1.

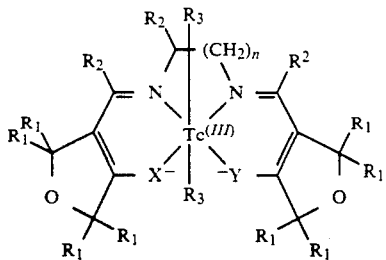

FORMULA 1

The $R_1$ groups illustrated in Formula 1 may be the same or different selected from the group consisting of hydrogen, hydroxy, $C_1$-$C_5$ alkyl—such as for example methyl or ethyl whereby methyl is preferred to decrease lipophilicity, and $C_1$-$C_5$ alkyl substituted by one or more members of the group consisting of hydroxy, ether—such as for example methoxymethyl or methoxyethyl whereby methoxymethyl is preferable to decrease lipophilicity, ester—such as for example methoxycarbonyl or phenoxycarbonyl whereby methoxycarbonyl is preferable to increase susceptibility to hydrolysis, amide—such as for example dimethylaminocarbonyl or aminocarbonyl, ketone—such as for example 2-propanoyl or 3-butanoyl, aldehyde—such as for example 1-propanoyl or 1-butanoyl and nitrile—such as for example cyanomethyl or cyanopropyl; and n may equal 1 or 2.

The $R_2$ groups illustrated in Formula 1 may be the same or different selected from the group consisting of hydrogen, hydroxy, $C_1$-$C_5$ alkyl—such as for example methyl or ethyl whereby methyl is preferred to decrease lipophilicity, and $C_1$-$C_5$ alkyl substituted by one or more members of the group consisting of hydroxy, ether—such as for example methoxymethyl or methoxyethyl whereby methoxymethyl is preferable to decrease lipophilicity, ester—such as for example methoxycarbonyl or phenoxycarbonyl whereby methoxycarbonyl is preferable to increase susceptibility to hydrolysis, amide—such as for example dimethylaminocarbonyl or aminocarbonyl, ketone—such as for example 2-propanoyl or 3-butanoyl, aldehyde—such as for example 1-propanoyl or 1-butanoyl and nitrile—such as for example cyanomethyl or cyanopropyl; and n may equal 1 or 2.

The X and Y groups may be the same or different selected from the group consisting of oxygen and sulfur.

The $R_3$ groups may be the same or different phosphine ligands of the following general Formula 2:

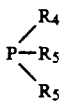

FORMULA 2

The $R_4$ group illustrated in Formula 2 is selected from the group consisting of hydrogen, $C_1$-$C_5$ alkyl—such as methyl or ethyl whereby methyl is preferred to decrease lipophilicity, ether—such as methoxymethyl or methoxyethyl whereby methoxymethyl is preferred to decrease lipophilicity, $C_1$-$C_5$ alkylaryl—such as phenylmethyl or phenylpropyl whereby phenylmethyl is preferred to decrease lipophilicity, and $C_1$-$C_5$ dioxanylpropyl, The $R_5$ groups may be the dioxanylmethyl or dioxanylpropyl. The $R_5$ groups may be the same or different from the $R_4$ group selected from a group consisting of $C_1$-$C_5$ alkyl—such as methyl or ethyl whereby methyl is preferred to decrease lipophilicity, ether—such as methoxymethyl or methoxyethyl whereby methoxymethyl is preferred to decrease lipophilicity, $C_1$-$C_5$ alkylaryl—such as phenylmethyl or phenylpropyl whereby phenylmethyl is preferred to decrease lipophilicity, and $C_1$-$C_5$ dioxanylalkyl—such as for example dioxanylmethyl or dioxanylpropyl. Examples of such phosphine ligands include but are not limited to tris (3-ethoxypropyl) phosphine (TEPP), trimethylphosphine (PMe$_3$), triethylphosphine (PEt$_3$), tris (3-methoxy-3-methylbutyl) phosphine (PR$_3$), tris (3-methoxypropyl) phosphine (TMPP), tris [2-[2-(1, 3-dioxolanyl)]ethylphosphine, tris 2-[2-(1,3-dioxolanyl)]ethyl]phosphine; methylbis (3-methoxypropyl) phosphine, tris (4-methoxy-butyl) phosphine (TMBP), dimethyl (3-methoxy-propyl) phosphine (L), and methylbis[2-[2-(1,3-dioxanyl]ethyl]phosphine.

Preferred phosphine ligands, also referred to as the "axial ligands", represented by $R_3$ in Formula 1 are tris(3-methoxypropyl)phosphine (TMPP) and tris[2-[2-(1,3-dioxanyl)]]ethylphosphine.

The technetium compounds of the present invention are bonded generally to three ligands, two axial phosphine ligands as just described (represented as $R_3$ in Formula 1, and more specifically illustrated in Formula 2), and a tetradentate equatorial ligand as generally described in Formula 1, and more specifically consisting of one of the following formulas:

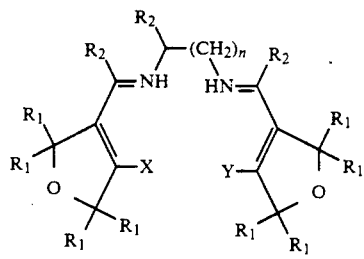

FORMULA 3

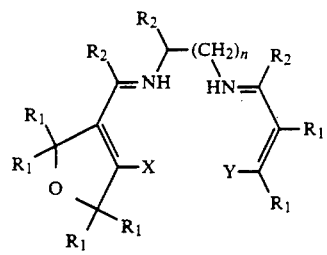

FORMULA 4

The $R_1$ groups and X groups for each of the equatorial ligands illustrated by Formulas 3 and 4 are the same as the R and X groups previously defined in Formula 1 above, and n likewise equals 1 or 2.

Examples of such tetradentate equatorial ligands of Formulas 3 and 4 are 1,2-Bis[dihydro-2,2,5,5-tetramethyl-3(2H)-furanone-4-methylene-amino]ethane, as illustrated by Formula 3, wherein the $R_1$ groups all represent hydrogen, n=1 and the X groups represent oxygen; 1-[Dihydro-2,2,5,5-tetramethyl-3(2H)-furanthione-4-methyleneamino]-2-[dihydro-2,2,5,5-tetramethyl-3(2H)-furanthione-4-methyleneamino]-2-[dihydro-2,2,5,5-tetramethyl-3(2H)-furanone-4-methyleneamino]ethane, as illustrated by Formula 3, wherein the $R_1$ groups all represent hydrogen, n=1 and the X groups represent oxygen and sulfur; 1,2-Bis[dihydro-2,2,5,5-tetramethyl-3(2H)-furanthione-4- methyleneamino]-ethane, as illustrated by Formula 3, wherein the $R_1$ groups all represent hydrogen, n=1 and the X groups represent sulfur; and butanoic acid, 2-[[[dihydro-2,2,5,5-tetramethyl-3(2H)furanone-4-methyleneamino]ethyl]amino]-methylene-3-oxoethylester as illustrated by Formula 4 wherein the $R_1$ groups all represent hydrogen, n=1 and the X groups represent oxygen.

Another equatorial ligand found to be useful is 2-Ethoxy-2-methyl-4-penten-3-one,5-5'-(1,2-ethanediyldiimino)bis.

Preferred equatorial ligands are 1,2-Bis[dihydro2,2,5,5-tetramethyl-3(2H)-furanone-4-methyleneamino]ethane, 1-[dihydro-2,2,5,5-tetramethyl-3(2H)-furanthione-4-methyleneamino]-2-(dihydro-2,2,5,5-tetramethyl-3(2H)-furanone-4-methyleneamino]ethane, and 1,2-Bis[dihydro-2,2,5,5-tetramethyl-3(2H)-furanthione-4-methyleneamino]ethane.

The preferred complexes of the present invention include trans-[1,2-bis[dihydro-2,2,5,5-tetramethyl-3(2H)-furanone-4-methyleneamino]ethane]bis-[tris(3-methoxypropyl)phosphine]-technetium-99m(III), trans-[1,2-bis[dihydro-2,2,5,5-tetramethyl-3(2H)-furanthione-4-methyleneamino]ethane]bis-[tris(3-methoxypropyl)-phosphine]-technetium-99m(III), trans-[1,2-bis[dihydro-2,2,5,5-tetramethyl-3(2H)furanone-4-methyleneamino]ethane]bis-[bis(3-methoxypropyl)-phosphine]technetium-99m(III), trans-[1,2-bis[dihydro-2,2-dimethyl-3(2H)-furanthione-4methyleneamino]ethane]bis[tris(3-methoxypropyl)phosphine]techne-tium-99m(III), trans-[1-[dihydro-2,2,5,5- tetramethyl-3(2H)furanthione-4-methyleneamino]-2-[dihydro2,2,5,5-tetramethyl-3(2H)furanone-4-methyleneamino]-ethane]-bis[bis(3-methoxypropyl)methylphosphine]-technetium-99m(III),trans-[1-[dihydro-2,2,5,5-tetramethyl3(2H-)furanthione-4-methyleneamino]-2-[dihydro-2,2,5,5-tetramethyl-3(2H)-furanone-4-methyleneamino]ethane]-bis[(3methoxypropyl)dimethylphosphine]technetium-99m(III), and trans-[1-[dihydro-2,2,5,5-tetramethyl-3 (2H)-furanthione-4methyleneamino]-2-[dihydro-2,2,5,5-tetramethyl-3(2H)-furanone-4-methyleneamino]ethane]bis[tris(2-(2-(l,3dioxanyl))]ethylphosphine]technetium-99m(III).

Each of the above $^{99m}$Tc(III) complexes shows significantly improved biodistribution and improved positive human heart images for use in diagnosis due to the presence of at least one furanose ring on the equatorial ligand. Examples of the above $^{99m}$Tc(III) complexes are listed in Table 1 illustrating the significantly improved biodistribution characteristic to this particular class of complexes. (See Table 1.)

TABLE 1

| Biodistribution Data of Selected Tc-99m (III) Complexes in Guinea Pigs | | | | |
|---|---|---|---|---|
| Tc-99m (III) Complex | Time (min) | % Heart uptake* | Heart/Liver | Heart/Blood |
| I | 5 | 0.8 | 1.5 | 4.6 |
| I | 60 | 0.9 | 6.6 | 35.6 |
| II | 5 | 0.9 | 1.6 | 6.1 |
| II | 60 | 0.8 | 5.6 | 26.5 |
| III | 5 | 1.1 | 0.9 | 5.9 |
| III | 60 | 1.0 | 1.5 | 3.5 |
| IV | 5 | 0.8 | 1.2 | 5.4 |
| IV | 60 | 0.9 | 3.0 | 58.6 |

*%Injected dose/Organ
I = trans-[1,2-bis[dihydro-2,2,5,5-tetramethyl-3(2H)furanone-4-methyleneamino]ethane]bis[tris(3-methoxypropyl)phosphine]technetium-99m (III)
II = trans-[1-[dihydro-2,2,5,5-tetramethyl-3(2H)furanthione-4-methyleneamino]-2-[dihydro-2,2,5,5-tetramethyl-3(2H)furanone-4-methyleneaminoethane]bis[tris(3-methoxypropyl)phosphine]technetium-99m (III)
III = trans-[1,2-bis[dihydro-2,2,5,5-tetramethyl-3(2H)furanthione-4-methyleneamino]ethane]bis[tris(3-methoxypropyl)phosphine]technetium-99m (III)
IV = trans-[1,2-bis[dihydro-2,2,5,5-tetramethyl-3(2H)furanone-4-methyleneamino]ethane]bis[tris(2-(2-(1,3-dioxanyl))]ethylphosphine]technetium-99m (III)

dro-2,2,5,5-tetramethyl-3(2H)-furanone-4-methyleneamino]ethane]bis-[tris(2-(2-(1,3-dioxanyl))]ethylphosphine]technetiumm-99m(III), trans-[1-[dihydro-2,2,5,5-tetramethyl-3(2H)-furanthione-4-methyleneamino]-2-[dihydro-2,2,5,5-tetra-methyl-3(2H)-furanone-4-methyleneamino]ethane]bis[tris(3-methoxy-propyl)phosphine]technetium-99m(III), trans-[1,2-bis[dihydro-2,2,5,5-tetramethyl-3(2H)-furanthione-4-methyleneamino]ethane]bis[tris(2-(2-(l,3dioxanyl))]ethylphosphine]technetium-99m(III), trans-[1,2-bis[dihydro-2,2,5,5-tetramethyl-3(2H)furanone-4-methyleneamino]ethane]bis[bis(3-methoxypropyl)methylphosphine]technetium-99m(III), trans-[1,2-bis[dihydro-2,2-dimethyl-3(2H)furanone-4-methyleneamino]ethane] bis[tris(3-methoxypropyl)-phosphine]-technetium-99m(III), trans-[1,2-bis[dihydro-2,2-dimethyl-3(2H)furanone-4-methyleneamino]ethane]bis[tris(4-methoxybutyl)phosphine]technetium-99m(III), trans-[1,2-bis[dihydro-2,2,5,5-tetramethyl-3(2H)furanone-4-methyleneamino]ethane]bis-[(3-methoxypropyl)-dimethylphosphine]technetium-99m(III), trans-[1,2-bis[dihydro-2,2,5,5-tetramethyl-3(2H)furanone-4-methyleneamino]ethane]bis[trimethylphosphine]- technetium-99m(III),trans-[1,2-bis[dihy- The myocardial imaging agents of the present invention may be made according to the following general examples:

A. General two step synthesis of technetium-99m(III) complexes of the present invention.

10–18 mg of the tetradentate equatorial ligand was dissolved in 0.1 mL of ethanol. A solution of 0.1 mL of $^{99m}$TcO$_4^-$ in saline (obtained from a molybdenum generator), diluted with 0.9 mL of water, was added and the mixture was deareated for 15 min. with argon. A solution of 30 microliters of 1M KOH and 15 micrograms of stannous chloride (in 5 microliters of ethanol, were added. The mixture was heated for 15 min. at 70° C. and cooled to room temperature. The reaction was monitored by HPLC on a PRP-1,250×4.1 mm, 10 micron column in 80:20 MeOH:H$_2$O (50 mM NH$_4$OAc) at a flow rate of 1.5 mL/min. 0.01–0.03 mmol of phosphine as its hydrochloride salt was added and the solution was heated for 15 min. at 70° C. and cooled to room temperature. The reaction mixture was purified by HPLC on a PRP-1,250×4.1 mm, 10 micron column in 80:20 MeOH:H$_2$O (50 mM NH$_4$OAc)-95:5 MeOH:H$_2$O (50 mM NH4OAc) at a flow rate of 1.5 mL/min. The HPLC eluate was diluted to 6.0–8.0 mL with the addition of 0.9% sodium chloride to give a solution of the technetium-99m(III) complex ready for use. The radiochemical purity was determined by HPLC on a PRP-1,150×4.1 mm, 10 micron column in 45:55 CH$_3$CN:0.1M NH$_4$OAc at a flow rate of 2.0 mL/min.

B. General one step synthesis of technetium-99m(III) complexes of the present invention.

2–5 mg of the tetradentate equatorial ligand was dissolved in 0.1 mL of ethanol, diluted with 1 mL of water and the mixture was deareated for 15 min. with argon. 0.05 mL of 0.1M KOH and 0.008 mL of stannous chloride solution (3 mg/mL in ethanol) were added. 0.001–0.01 mmol of phosphine as its hydrochloride salt was added. A solution of 0.1 mL of $^{99m}$TcO$_4^-$ in saline (obtained from a molybdenum generator) was added. The mixture was heated for 15 min. at 100° C. and cooled to room temperature to give a solution of the technetium-99m(III) complex ready for use. The radiochemical purity was determined by HPLC on a PRP-1,250×4.1 mm, 10 micron column in 45:55 CH$_3$CN:0.1M NH$_4$OAc at a flow rate of 2.0 mL/min.

The myocardial imaging agents of the present invention may be made according to the following specific examples:

EXAMPLE 1

Synthesis of 1,2-bis[dihydro-2,2,5,5-tetramethyl-3(2H)furanone-4-methyleneamino]ethane Mercuric oxide (600 mg) was dissolved in 200 mL of water containing 2 mL of concentrated H$_2$SO$_4$. Solid 2,5-dimethyl-3-hexyne-2,5-diol (50.0g, 352 mmol) was added and the solution was heated until the homogeneous solution turned cloudy. Heating was stopped and the flask was stirred in a room temperature water bath for 30 min. The solution was distilled and 250 mL of distillate was collected (more H$_2$O was added). The biphasic material was taken up into ether, separated, washed with brine, dried over MgSO$_4$, filtered, evaporated and distilled (150° C.) to give 44.5 g (89%) of dihydro-2,2,5,5-tetramethyl-3(2H)-furanone as a water-white oil. Dihydro-2,2,5,5-tetramethyl-3(2H)furanone (32.1 g, 226 mmol) in 50 mL of ether was added dropwise to a suspension of sodium hydride (18.1 g of 60%, 453 mmol) in 400 mL of ether containing two drops of ethanol and 36.5 mL (453 mmol) of ethyl formate stirred at 0° C. After stirring overnight at room temperature, the reaction mixture was taken up into water, washed with additional ether, acidified with 6N HCl and extracted into ether. The combined ether layers were washed with water and brine, dried over MgSO$_4$, decolorized with charcoal, filtered through celite and evaporated. The solid residue was recrystallized from a small volume of ether and a large quantity of hexanes. The solid was isolated by filtration and dried to give 30.4 g (79%) of 4-hydroxymethylene-dihydro-2,2,5,5-tetramethyl-3(2H)-furanone as an off-white solid. Ethylenediamine (1.15 mL, 17.4 mmol) was added to a solution of 4-hydroxymethylene-dihydro-2,2,5,5-tetramethyl-3(2H)furanone (5.9 g, 34.7 mmol) in 40 mL of THF. This solution was refluxed for one hour. The solvents were evaporated under high vacuum with moderate heating. The solid residue was slurried in 50 mL of cold ether and filtered to give 5.3 g (76%) of off-white solid. Recrystallization from 50 mL of THF followed by drying at 70° C. (1 Torr) for 6 hours gave 4.0 g of 1,2-bis[dihydro-2,2,5,5-tetramethyl3(2H)furanone-4-methyleneamino]ethane as a white solid: Anal. Calc'd for C$_{20}$H$_{32}$N$_2$O$_4$: C, 65.93; H, 8.79; N, 7.69. Found: C, 65.68; H, 8.90; N, 7.65.

EXAMPLE 2

Synthesis of 1,3-bis[dihydro-2,2,5,5-tetramethyl-(3(2H)furanone-4-methyleneamino]propane.

Propylenediamine (0.37 mL, 4.4 mmol) and 4-hydroxymethylene-dihydro- 2,2,5,5-tetramethyl-3(2H)-furanone(1.5 g, 8.8 mmol) were refluxed together in 25 mL of methanol for 10 min. The solvent was evaporated and the residue was chromatographed on the Chromatotron (4 mm, 8/2 EtOAc/hexanes). The clean fractions were evaporated to leave a solid. Recrystallization from EtOAc/hexanes gave 700 mg of 1,3-bis[dihydro-2,2,5,5-tetramethyl3(2H)furanone-4-methyleneamino]propane as a white solid. This material was dried overnight at 70° C. under high vacuum: mp 125°–127° C.; Anal. Calc'd for C$_{21}$H$_{34}$N$_2$O$_4$: C, 66.67; H, 8.99; N, 7.41. Found: C, 66.52; H, 9.03; N, 7.36.

EXAMPLE 3

Synthesis of 1,2-bis[dihydro-2,2,5,5-tetramethyl-3(2H)furanone-4methoxyethyleneamino]ethane A solution of dihydro-2,2,5,5-tetramethyl-3(2H)-furanone (5.0 g, 35 mmol) and methyl methoxyacetate (3.5 mL, 35 mmol) in 20 mL of ether was added dropwise to a suspension of sodium hydride (2.8 g of 60%, 70 mmol) in ice-cold ether (100 mL) containing two drops of ethanol. After the addition was complete, the ice-bath was removed and stirring was continued overnight. Water was added and the layers were separated. The brown aqueous layer was washed with ether, acidified with 3N HCl, and extracted with ether. The combined organic layers were washed with water and brine, dried over MgSO$_4$, filtered and evaporated to leave 1,6 g (21%) of 4-(2-hydroxy-l-methoxyethylene- dihydro-2,2,5,5-tetramethyl-3-(2H)furanone as an oil.

Crude 4-(2-hydroxy-l-methoxyethylene-dihydro-2,2,5,5-tetramethyl-3-(2H)furanone (1.6 g, 7.2 mmol) and ethylenediamine (0.25 mL, 3.6 mmol) were refluxed together in 25 mL of methanol for 5 min. Crystals formed within a few min. After cooling, the solid was isolated by filtration to give 1.47 g (90%) of cream colored solid. A 1.25 g portion was recrystallized from methanol to give 1.0 g of 1,2-bis[dihydro-2,2,5,5-tetramethyl-3(2H)-furanone-4methoxyethyleneamino]ethane as white crystals: MP 192°–194° C. (d); Anal. calc'd for C$_{24}$H$_{40}$N$_2$O$_6$.2H$_2$O: C, 59.02; H, 9.02; N, 5.74. Found: C, 58.91; H, 9.11; N, 5.80.

EXAMPLE 4

Synthesis of 1,2-bis[dihydro-2,2-dimethyl-3(2H)furanone-4-methyleneamino]ethane

Hydrogen gas was bubbled over the top of a mixture of 2,2-dimethyl-3(2H)furanone (5.0 g, 45 mmol) and 5% Pd/C (1.0 g) in 50 mL of water. After 24 hours, the starting material remained unchanged, so the mixture was transferred to a parr bottle and hydrogenated overnight at a pressure of 40 psi. The catalyst was removed by filtration and the aqueous solution was saturated with sodium chloride and extracted with ether. The combined ether layers were dried over MgSO$_4$, filtered and a large amount of the ether was distilled off through a short fractionating column to leave a 46 mol % or 56.5 wt % solution of dihydro-2,2-dimethyl-(3(2H)furanone in ether (4.55 g, 90%).

An ether solution of dihydro-2,2-dimethyl-3(2H)-furanone (4.55 g, 39.9 mmol) in 30 mL of ether was added dropwise to a suspension of sodium hydride (3.2 g of 60%, 80 mmol) in 150 mL of ether containing three drops of ethanol and 6.5 mL (80 mmol) of ethyl formate stirred at 0° C. After stirring overnight at room temperature, the reaction mixture was taken up into water, the ether layer separated, washed with additional ether, acidified with 6N HCl and with water and brine, dried over MgSO$_4$, decolorized with charcoal, filtered and evaporated to leave 2.4 g of 4-hydroxymethylene-dihydro-2,2-dimethyl-3(2H)furanone as a colorless oil (43%).

A solution of ethylenediamine (0.56 mL, 8.4 mmol) and 4-hydroxymethylene-dihydro-2,2-dimethyl-3(2H)furanone (2.4 g, 16.9 mmol) in 40 mL of methanol was refluxed for 5 min. The orange solution was evaporated. The residue was taken up into boiling ethyl acetate, decolorized with charcoal, filtered hot and evaporated. The residue was slurried in ether and filtered cold to give 2.0 g of yellow solid. A 1.5 g sample was recrystallized from THF/hexanes to give 1.0 g of yellow solid. This material was recrystallized from MeOH/ether to give 700 mg of 1,2-bis[dihydro-2,2-dimethyl -3(2H)furanone-4-methyleneamino]ethane as a light yellow solid after drying under high vacuum overnight at 100° C.: mp 171°–173° C.; Anal. Calc'd for C$_{16}$H$_{24}$N$_2$O$_4$: C, 62.34; H, 7.79; N, 9.09. Found: C, 62.19; H, 7.80; N, 9.06.

EXAMPLE 5

Synthesis of butanoic acid, 2-[[[dihydro-2,2,5,5-tetramethyl-3(2H)furanone-4-methyleneamino]ethyl]amino]-methylene-3-oxo ethyl ester Ethylenediamine (1.0 mL, 15 mmol) was added to 4-hydroxymethylene-2,2,5,5-tetramethyl-3(2H)furanone (750 mg, 4.4 mmol) in 20 mL of ethanol. After stirring for one hour excess ethylenediamine and ethanol were removed by evaporation. Additional ethanol (20 mL) was added followed by ethyl 2-ethoxymethylene-3-oxobutanoate (820 mg, 4.4 mmol) in 20 mL of ethanol. The solution was refluxed for 15 min. then cooled. The byproduct, butanoic acid, 2,2'-[1,2-ethanediylbis(iminomethylidyne)]-bis[3-oxo]-diethyl ester (300 mg) was removed by filtration. The filtrate was evaporated and chromatographed to give 666 mg (43%) of butanoic acid, 2-[[[dihydro-2,2,5,5-tetramethyl-3(2H)furanone-4-methyleneamino]ethyl]amino]-methylene-3-oxo-ethyl ester as a white solid.

EXAMPLE 6

Synthesis of 1,2-bis[dihydro-2,2,5,5-tetramethyl-3(2H)furanthione-4-methyleneamino]ethane A heterogeneous mixture of 1,2-bis[dihydro-2,2,5,5-tetramethyl-3(2H)-furanone-4-methyleneamino]ethane (1.0 g, 2.7 mmol) and Lawesson's Reagent ([2,4-bis(4-methoxyphenyl)-1,3-dithia-2,4-diphosphetane-2,4-disulfide],1.2 g, 3.0 mmol) was stirred in 35 mL of dimethoxyethane for 1 hour at room temperature. The solution became bright orange and homogeneous. The solution was poured into methylene chloride, washed with water and brine, dried over MgSO$_4$, filtered and evaporated. The solid residue was slurried in ether, cooled and the orange solid was collected (1.1 g). This material was chromatographed on the Chromatotron (4 mm 1/1 EtOAc/hexanes→EtOAc). The isolated pure fractions were evaporated and the residue was recrystallized from methylene chloride/hexanes to give 720 mg (66%) of 1,2-bis[dihydro-2,2,5,5-tetramethyl-3(2H)furanthione-4-methyleneamino]ethane as an orange solid: mp 219°–221° C.; Anal. Calc'd for C$_{20}$H$_{32}$N$_2$O$_2$S$_2$: C, 60.61; H, 8.08; N, 7.07; S, 16.16. Found: C, 60.35; H, 8.06, N, 7.03; S, 16.28.

EXAMPLE 7

Synthesis of 1,3-bis[dihydro-2,2,5,5-tetramethyl-3(2H)furanthione-4-methyleneamino]propane Propylenediamine (0.5 mL, 0.44 g, 6.0 mmol) and 4-hydroxymethylene-dihydro- 2,2,5,5-tetramethyl-3(2H)furanone (2.0 g, 12 mmol) were refluxed together in 30 mL of methanol for 10 min. The solvent was evaporated and the residue was crystallized from EtOAc/hexanes to give 1.7 g (76%) of white solid. This material was stirred with Lawesson's Reagent (2.0 g, 4.9 mmol) in 50 mL of DME for 30 min. at room temperature. The solvents were evaporated and the residue was diluted with methylene chloride and run through a short column of 1/1 silica/basic alumina (CH$_2$Cl$_2$). The yellow eluant was evaporated and the residue was recrystallized from CH$_2$Cl$_2$/hexanes to give 1.5 g (82%) of 1,3-bis[dihydro-2,2,5,5-tetramethyl-3(2H)furanthione-4-methyleneamino]propane as an orange solid: mp 172°–173° C.; Anal. Calc'd for C$_{21}$H$_{34}$N$_2$O$_2$S$_2$: C, 61.46; H, 8.29; N, 6.83; S, 15.61. Found: C, 61.21; H, 8.33; N, 6.76; S, 15.47.

EXAMPLE 8

Synthesis of 1,2-bis[dihydro-2,2-dimethyl-3(2H)-furanthione-4-methyleneamino]ethane A mixture of 1,2-bis[dihydro-2,2-dimethyl-3(2H)furanone-4-methyleneamino]ethane (1.0 g, 3.2 mmol) and Lawesson's Reagent (1.4 g, 3.5 mmol) was stirred in 35 mL of DME for 30 min. at room temperature. The mixture was cooled in an ice-bath for one hour to precipitate an orange solid that was collected by filtration. Recrystallization from chloroform/hexanes gave 460 mg (42%) of 1,2-bis[dihydro-2,2-dimethyl-3(2H)furanthione-4-methyleneamino]ethane as orange crystals: mp 210°–212° C.; Anal. Calc'd for C$_{16}$H$_{24}$N$_2$O$_2$S$_2$: C, 56.47; H, 7.06; N, 8.24; S, 18.82. Found: C, 56.41; H, 7.10; N, 8.22; S, 18.74.

EXAMPLE 9

Synthesis of 1-[dihydro-2,2,5,5-tetramethyl-3(2H)furanthione-4-methyleneamino]-2-[dihydro-2,2,5,5-tetramethyl-3(2H)furanone-4-methyleneamino]ethane Ethylamine gas was bubbled through a solution of 4-hydroxymethylene-dihydro-2,2,5,5-tetramethyl-3(2H)furanone (4.0 g, 24 mmol) in 50 mL of chloroform at room temperature for 15 min. The solvents were evaporated and the residue was recrystallized from hexanes to give 3.0 g (65%) of dihydro-2,2,5,5-tetramethyl-4-ethylaminomethylene-3(2H)furanone as a light brown solid.

A mixture of dihydro-2,2,5,5-tetramethyl-4-ethylaminomethylene-3(2H)furanone (1.0 g, 5.1 mmol) and Lawesson's Reagent (1.1 g, 2.7 mmol) was stirred in 20 mL of DME for 20 min. at room temperature. The solvent was evaporated and the residue was dissolved in methylene chloride and eluted through a plug of silica gel/basic alumina 1/1 ($CH_2Cl_2$). The eluant was evaporated to leave dihydro-2,2,5,5-tetramethyl-4-ethylaminomethylene-3(2H)furanthione as an orange solid.

Ethylenediamine (2.2 mL, 2.0 g, 33 mmol) was added to an ice-cold solution of 4-hydroxymethylene-dihydro-2,2,5,5-tetramethyl-3(2H)furanone (1.6 g, 9.4 mmol) in 40 mL of chloroform. After 15 min. at room temperature, the solvent and excess ethylenediamine were removed by evaporation. The residue was diluted with 50 mL of ethanol, 2.0 g (9.4 mmol) of dihydro-2,2,5,5-tetramethyl-4ethylaminomethylene-3-(2H)furanthione was added and the solution was refluxed for 30 min. The solvent was evaporated and the residue was chromatographed in two portions on the chromatotron (4 mm, 1 Hex/EtOAc (5% TEA)). The clean fractions of both runs were combined to give 1.33 g (36%) of yellow solid. An 800 mg fraction of this product was chromatographed in two portions (350 & 450 mg) on a Phenomenex 500×22.5 mm Partisil 10 column using the Waters 3000 (mobile phase 1/1 EtOAc (5% TEA)/hexane), injection volume ~1.0 mL in $CH_2Cl_2$, flow rate 15 mL/min, fractions collected starting at ~60 min). The early eluting clean fractions of both runs were combined and evaporated to give 700 mg of yellow solid. Recrystallization from $CH_2Cl_2$/hexanes and drying 4 hours at 60° C. gave 550 mg of 1-[dihydro-2,2,5,5-tetramethyl-3(2H)furanthione-4-methyleneamino]-2-[dihydro-2,2,5,5-tetramethyl-3(2H)furanone-4-methyleneamino]ethane as yellow crystals: mp 122°–125° C. Anal. Calc'd for $C_{20}H_{32}N_2O_3S$: C, 63.16; H, 8.42; N, 7.37; S, 8.42. Found: C, 63.18; H, 8.51; N, 7.39; S, 8.53.

EXAMPLE 10

Synthesis of 1-[dihydro-2,2,5,5-tetramethyl-3(2H)furanthione-4-methyleneamino]-3-[dihydro-2,2,5,5-tetramethyl-3(2H)furanone-4-methyleneamino]propane Propylenediamine (1.4 mL, 1.2 g, 17 mmol) was added to an ice-cold solution of 4-hydroxymethylene-dihydro-2,2,5,5-tetramethyl-3(2H)furanone (0.8 g, 4.7 mmol) in 20 mL of chloroform. After 10 min. at room temperature, the solvent and excess propylenediamine were removed by evaporation to leave a thick oil. The residue was diluted with 30 mL of ethanol and 1.0 g (4.7 mmol) of dihydro-2,2,5,5-tetramethyl-4-ethylaminomethylene-3(2H)furanthione was added. The solution was refluxed for two hours. The solution was evaporated and the residue was chromatographed on the Chromatotron (4 mm, 7/3 Hexanes/EtOAc (5% TEA)) to give 400 mg of crude O,S product. This fraction was rechromatographed (7/3 hexanes/$CH_2Cl_2$, 5% MeOH) and the clean fractions were combined, evaporated and recrystallized from $CH_2Cl_2$/hexanes to give 200 mg of 1-[dihydro-2,2,5,5-tetramethyl-3(2H)furanthione-4 -methyleneamino]- 3-[dihydro-2,2,5,5-tetramethyl-3(2H)furan one-4-methyleneamino]propane as a yellow solid: mp 129°–130° C.; Anal. Calc'd for $C_{21}H_{34}N_2O_3S$: C, 63.96; H, 8.63; N, 7.11; S, 8.12. Found: C, 63.81; H, 8.68; N, 7.06; S, 8.14.

EXAMPLE 11

Synthesis of 1-[dihydro-2,2,5,5-tetramethyl-3(2H)furanthione-4-methyleneamino]-2-[2-propane-3-ethyleneamino]ethane Methylamine gas was bubbled through a solution of 4-hydroxymethylene-dihydro-2,2,5,5-tetramethyl-3(2H)furanone (5.0 g, 29 mmol) in 50 mL of chloroform for 30 min. The solvents were evaporated. The solid residue was recrystallized from hexanes to give 4.0 g (74%) of dihydro-2,2,5,5-tetramethyl-4-methylaminomethylene-3(2H)furanone as a light yellow solid: mp 80°–82° C.; Anal Calc'd for $C_{10}H_{17}NO_2$: C, 65.57; H, 9.29; N, 7.65. Found: C, 65.47; H, 9.30; N, 7.60.

A mixture of dihydro-2,2,5,5-tetramethyl-4-methylaminomethylene-3(2H)furanone (3.2 g, 18 mmol) and Lawesson's Reagent (3.8 g, 9.4 mmol) in 40 mL of DME was stirred for 30 min. at room temperature. The solvents were evaporated from the homogeneous orange solution. The residue was taken up in a small volume of methylene chloride and eluted through a short column of 1/1 silica gel/basic alumina with methylene chloride. The solvent was evaporated to leave a yellow solid. Recrystallization from $CH_2Cl_2$/hexanes gave 2.5 g of dihydro-2,2,5,5-tetramethyl-4-methylaminomethylene-3(2H)furanthione as an orange solid. An analytically pure sample was made by chromatographing a small amount on the Chromatotron (Silica 1/1 EtOAc/hexanes): mp 115°–117° C.; Anal. Calc'd for $C_{10}H_{17}NOS$: C, 60.30; H, 8.54; N, 7.04; S, 16.08. Found: C, 60.27; H, 8.62; N, 7.04; S, 16.15.

Acetylacetone (0.5 g, 5 mmol) in 10 mL of chloroform was added dropwise to a room temperature solution of ethylenediamine (1.0 mL, 15 mmol) in 10 mL of chloroform. After three hours the excess ethylenediamine and solvent were removed by evaporation. The oily residue was dissolved in 20 mL of ethanol. Dihydro-2,2,5,5-tetramethyl-4-methylaminomethylene-3(2H)furanthione (1.0 g, 5 mmol) was added and the solution was refluxed for 15 min. and the solvents evaporated. The residue was chromatographed on the Chromatotron (4 mm 3/2 Hexanes/EtOAc (5% TEA)). The clean fractions were combined and evaporated. The solid residue was slurried in cold hexanes, filtered and dried to give 222 mg of 1-[dihydro-2,2,5,5-tetramethyl-3(2H)furanthione-4-methyleneamino]2-[2-propane-3-ethyleneamino]ethane as a yellow solid: mp 163°–166° C.; Anal. Calc'd for $C_{16}H_{26}N_2O_2S$: C, 61.94; H, 8.39; N, 9.03; S, 10.32. Found: C, 61.89; H, 8.48; N, 8.98; S, 10.24.

EXAMPLE 12

Synthesis of (2S)-2,3-bis[dihydro-2,2,5,5-tetramethyl-3(2H)furanone-4-methyleneamino]propanoate, ethyl ester A mixture of ethyl (2S)-2,3-diaminopropanoate dihydrochloride (2.8 g, 14 mmol), 4-hydroxymethylene-dihydro-2,2,5,5-tetramethyl-3(2H)furanone (4.6 g, 27 mmol) and triethylamine (4.1 mL, 31 mmol) was refluxed in 50 mL of ethanol for 10 min. The solvents were evaporated and the residue was taken up into ether, washed with water and brine, dried over $MgSO_4$, filtered and evaporated to leave 4.6 g (77%) of yellow glass. A one gram portion of the crude product was chromatographed on silica gel (7/3 hexanes/ethyl acetate-1/1) to give after trituration with hexanes and recrystallization from ether/hexanes 570 m of (2S)-2,3-bis[dihydro-2,2,5,5-tetramethyl-3(2H)furanone-4-methyleneamino]propanoate, ethyl ester as a white solid: mp=95°-96° C. ; Anal. Calc'd for $C_{23}H_{36}N_2O_6$: C, 63.30; H, 8.26; N, 6.42. Found: C, 63.24; H, 8.33; N, 6.38.

EXAMPLE 13

Synthesis of 1-[5,5-dimethyl-2,4-(3H,5H)furandione-3-methyleneamino]-2-[dihydro-2,2,5,5-tetramethyl-3(2H)-furanone-4-methyleneamino]ethane Dimethylformamide dimethylacetal (10.4 mL, 78 mmol) and 5,5-dimethyl-tetronic acid (5.0 g, 39 mmol) were stirred together overnight at room temperature. Ether (25 mL) was added and after cooling in an ice-bath the solid was collected by filtration.

Recrystallization from ethyl acetate/hexanes gave 6.2 g (86%) of 3-dimethylaminomethylene-5,5-dimethyl tetronic acid as a bright yellow solid.

Hydroxymethylene-2,2,5,5-tetramethyl-3(2H)furanone (1.0 g, 5.9 mmol) was added to a solution of ethylenediamine (1.2 mL, 18 mmol) in 20 mL of ethanol. After one hour, the excess ethylenediamine and solvent were evaporated. The residue was dissolved in 20 mL of ethanol and 3-dimethylaminomethylene-5,5-dimethyl tetronic acid (1.1 g, 5.9 mmol) was added. The mixture was refluxed for ten minutes then cooled. The solid was collected by filtration and recrystallized from ethanol and dried to give 900 mg (44%) of 1-[5,5-dimethyl-2,4-(3H,5H)furandione-3-methyleneamino]-2-[dihydro-2,2,5,5-tetramethyl-3(2H)furanone-4-methyleneamino]ethane as a white solid; mp 225°-227° C. Anal Calc'd for $C_{18}H_{26}N_2O_5$; C, 61.71; H, 7.43; N, 8.00. Found: C, 61.68; H, 7.49; N, 8.00.

EXAMPLE 14

Synthesis of tris[2-[2-(1,3-dioxanyl)]ethyl]phosphine

2-[2-(1,3-dioxanyl)]ethylmagnesium bromide was generated from 2-(2-bromoethyl)-1,3-dioxane (15.0 g, 76.9 mmol) and Mg metal (1.9 g, 76.9 mmol) and reacted with $PCl_3$ (1.1 ml, 12.8 mmol) according to General Method I. The residue was recrystallized (2x) from methanol to afford 4.16 g (86%) of tris[2-[2-(1,3-dioxanyl)]ethyl]phosphine as white needles. $^{31}$P-NMR $(CDCl_3)$:δ-29.6. MS (LREI) m/z=376. Anal. Calcd. for $C_{18}H_{33}O_6P$: C 57.43, H 8.84, P 8.23. Found: C 57.42, H 8.85 P 8.37.

GENERAL METHOD I

To ground Mg (100 mmol) in THF (25 ml) was added 1 crystal $I_2$ and 1 drop of 1,2-dibromoethane followed by several drops of halide (100 mmol) in THF (25 ml) and the reaction was initiated by warming. The remaining halide/THF solution was added at a rate which maintained a gentle reflux. The reflux was continued for 2 h post-addition by external heating. The material was diluted with THF (50 ml), cannula transferred (away from unreacted Mg metal) to a fresh dry flask under Argon, cooled to −78° C. and stirred for 30 min. $PX_3$ (15 mmol) in THF (5 ml) was added dropwise over 1 h, allowed to warm to $R_4$ T., gradually, and heated to reflux for 2 h thereafter. The reaction was cooled to 10° C. and quenched by dropwise addition of deaerated water (10 ml). The THF solution was cannula transferred onto 20 g of $Na_2SO_4$, allowed to dry for 6 h and cannula transferred to a fresh flask. The THF was removed by distillation and the residue was purified by distillation or recrystallization a indicated.

EXAMPLE 15

Synthesis of tris[2-[2-(1,3-dioxolanyl)]ethyl]phosphine

2-[2-(1,3-dioxolanyl)]ethylmagnesium bromide was generated from 2-(2-bromoethyl)I,3-dioxolane (15.0 g, 83.0 mmol) and Mg metal (2.1 g, 86.0 mmol) and reacted with $PCl_3$ (0.9 ml, 10.3 mmol) according to General Method I. The residue was distilled (kugelrhor) to provide 1.26 g (36%) of tris[2-[2-(1,3-dioxolanyl)]ethyl]phosphine as a colorless mobile oil. $^{31}$PNMR$(CDCl_3)$ δ-29.8.

EXAMPLE 16

Synthesis of tris(3-methoxypropyl)phosphine

Mechanically stirred 1,3-propanediol (1500 g, 19.7 mol) is heated to 80° C. and solid KOH (735 g, 13.1 mol) is added in portions over 1h. The mixture is stirred for 1h post-addition, the apparatus is fitted with an efficient condenser and methyl iodide (815 ml, 13.1 mol) is added dropwise over 12h. The mixture is stirred for 6h post-addition at 80° C. and allowed to cool. The solids are filtered and the filtrate is extracted with chloroform (3×500 ml). The combined extracts are thoroughly dried with $Na_2SO_4$ and concentrated. Fractional distillation afforded 466 g (40%) of pure 3-methoxy-propanol:(bp=149° C.@1 atm).

3-Methoxypropanol (238.5 g, 2.6 mol) was dissolved in pyridine (206 g), cooled to 5° C., and thionyl chloride (284 ml, 3.9 mol) was added dropwise over 2h with vigorous mechanical stirring. When the addition was complete the reaction mixture was refluxed for 3h and poured onto 1 kg crushed ice in conc. HCl (200 ml). The layers are separated and the organic portion is dried over $K_2CO_3$. Concentration and purification of the residue by fractional distillation (bp=110° C.@1 atm) afforded 161.5 g (57%) of pure 1-chloro-3-methoxypropane as a colorless liquid.

3-Methoxypropyl-magnesium chloride was generated from 1-chloro-3-methoxypropane (20.0 g, 184 mmol) and magnesium metal (4.48 g, 184 mmol) and reacted with dichloroethoxy-phosphonite (3.50 ml, 30.7 mmol) according to
General Method I. Vacuum distillation (bp.=154°-155° C.@2.4 mm Hg) afforded 3.80 g (49%) of tris(3 methoxypropyl)-phosphine as a colorless mobile oil. $^{31}$P-NMR (Benzene-$d_6$): δ −32.9. MS (LREI) m/z=251 (M+1).

EXAMPLE 17

Synthesis of tris(4-methoxybutyl)phosphine

4-Methoxybutylmagnesium chloride was generated from 1-chloro-4-methoxybutane (7.0 g, 57.1 mmol) and magnesium metal (1.4 g, 57.1 mmol) and reacted with $PCl_3$ (0.83 ml, 9.5 mmol) according to General Method I. Vacuum distillation (146° C.@1.05 mm Hg) afforded 2.10 g (76%) of tris(4-methoxybutyl)phosphine as a colorless mobile oil. $^{31}$P-NMR (Benzene-$d_6$): −28.9. MS (LREI) m/z=293 (M+I).

EXAMPLE 18

Synthesis of tris(3-ethoxypropyl)phosphine

To 3-ethoxypropanol (50,0 g, 0.48 mol) in pyridine (250 ml) was added benzenesulfonyl chloride (67.4 ml, 0.53 mol) dropwise at 0° C. The mixture was allowed to warm to RT and stir over night. The mixture was poured into cold 6N HCl (200 ml) and the resulting mixture was extracted with ether (3×100 ml). The combined extracts were dried (Na$_2$SO$_4$) and concentrated and the crude oil was immediately dissolved in acetone (300 ml) and treated with LiCl (23.5 g). After stirring at RT for 12 h the solution was poured into water (500 ml) and extracted with pentane (3×200 ml). The combined extracts were dried (Na$_2$SO$_4$) and concentrated. The residue was purified by fractional distillation affording 52.0 (88%) of pure 1-chloro-3-ethoxypropane as a colorless liquid.

3-Ethoxypropylmagnesium chloride was generated from 1-chloro-3-ethoxypropane (10 g, 81.6 mmol) and Mg metal (2 g, 81.6 mmol) and reacted with PCl$_3$ (0.89 ml, 10.2 mmol) according to General Method I. Vacuum distillation of the residue afforded 2.2 g (74%) of tris(3-ethoxypropyl)-phosphine as a mobile colorless oil (b.p.=120° C.@0.15 mmHg). $^{31}$P-NMR (CDCl$_3$):δ −31.3. MS (LRCI) m/z=309 (M+16; phosphine oxide).

EXAMPLE 19

Synthesis of tris(2-methoxyethoxymethyl)phosphine

To ground Mg metal (5.2 g, 214 mmol) was added I$_2$ (1 crystal), HgBr$_2$ (10 mg) and 2 ml of a solution of 2-methoxyethoxymethyl chloride (25 g, 201 mmol) in THF (100 ml) at R.T. After 30 sec, the reaction started and was cooled to −30° C. (dry-ice/acetone). The remaining chloride/THF solution was added dropwise at −20° to −10° C. over 2 h. The mixture was stirred at 0° C. for 2h post-addition and cooled to −78° C. The reagent was then treated with PCl$_3$ (2.2 ml, 25.1 mmol) according to General Method I and the final residue was purified by distillation to afford 1.6 (21%) of tris(2-methoxyethoxymethyl)phosphine as a colorless mobile oil (b.p.=150°-160° C.@1.1 mmHg). $^{31}$P-NMR(CDCl$_3$): −42.7. MS(LREI)m/z=299(M+1).

EXAMPLE 20

Synthesis of tris(3-methoxy-3-methylbutyl)phosphine

To isoprenyl alcohol (80.0 g, 929 mmol) in CH$_2$Cl$_2$(500 ml) at 0° C. was added one drop of methanesulfonic acid. To this solution was added 2,3-dihydropyran (100 ml, 1.10 mol) dropwise over 3 h. After the addition was complete triethylamine (5 ml) was added and the resulting mixture was filtered through a thin pad of SiO$_2$ and concentrated to afford 159 g (100%) of 2-(3-methyl-3-butenyloxy)tetrahydropyran as a colorless liquid.

To 2-(3-methyl-3-butenyloxy)tetrahydropyran (150.0 g, 881.0 mmol) in methanol (600 ml) was added mercuric acetate (309 g, 969 mmol) and the mixture was stirred until it became homogeneous. To this solution was added 0.5N NaOH (500 ml) in one portion followed by dropwise addition of 0.5N NaBH$_4$ in 0.5N NaOH (500 ml). The mixture is stirred until mercury metal congeals at the bottom of the flask. The solution is decanted into a separatory funnel and extracted with ether (3×300 ml). The combined ethereal extracts are dried (MgSO$_4$) and concentrated to afford 166 g (93%) of 2-(3-methoxy-3-methylbutyloxy)tetrahydropyran as a colorless liquid.

2-(3-Methoxy-3-methylbutyloxy)tetrahydropyran (166 g, 821 mmol) was dissolved in methanol (500 ml) and treated with Dowex-55 strong acid resin (100 g). The reaction was stirred at RT until TLC indicated no starting material remaining. The mixture was filtered and thoroughly concentrated to afford 92 g crude alcohol. This material was azeotropically dried by rotovaping with toluene (2×100 ml) and a 10.2 g (86.3 mmol) aliquot was dissolved in pyridine (75 ml). The solution was cooled to 0° C. and benzenesulfonyl chloride (12.7 ml, 99.3 mmol) was added dropwise. The reaction was stirred for 12 h at RT and poured into cold water (500 ml). The resulting mixture was extracted with ether (3×50 ml) and the combined extracts are dried (Na$_2$SO$_4$) and concentrated. The crude oil was immediately dissolved in acetone (200 ml) and treated with LiCl (10.0 g, 236 mmol). The mixture was stirred for 6h filtered and concentrated. The residue was dissolved in water (500 ml) and extracted with pentane (3×50 ml). The combined extracts were dried (MgSO$_4$), concentrated and distilled (Kugelrhohr) to afford 8.70 g (78%) of pure 1-chloro-3-methoxy-3-methylbutane.

3-Methoxy-3-methylbutylmagnesium chloride was generated from 1-chloro-3-methoxy-3-methylbutane (8.0 g, 58.6 mmol) and Mg metal (1.43 g, 58.6 mmol) and reacted with PCl$_3$ (0.6 ml, 7.3 mmol) according to General Method 1. The residue was purified by distillation to afford 1.66 g (68%) of pure tris(3-methoxy-3-methylbutyl)phosphine as a colorless viscous oil. $^{31}$PNMR (CD$_3$OD):δ −26.3. MS (HRFAB) m/z=335.2724 (M+1); (335.2719 calc'd for C$_{18}$H$_{40}$O$_3$P).

EXAMPLE 21

Synthesis of 3-methoxypropyldimethylphosphine

3-Methoxypropyl-magnesium chloride was generated from 1-chloro-3-methoxypropane (8.0 g, 74 mmol) and Mg metal (1.8 g, 74 mmol) and reacted with dimethylchlorophosphine (3.6 g, 37 mmol) according to General Method I. The residue was purified by fractional distillation (bp=89°-90° C.@103 mm Hg) to afford pure 3-methoxypropyldimethylphosphine as a colorless liquid. $^{31}$PNMR (Benzene-d$_6$):δ −53.5. MS (HREI) m/z=134.0858 (134.0860 calc'd for C$_6$H$_{15}$OP).

EXAMPLE 22

Synthesis of bis(3-methoxypropyl)methylphosphine

3-Methoxypropyl-magnesium chloride was generated from 1-chloro-3-methoxypropane (10.0 g, 92.0 mmol) and Mg metal (2.26 g, 93.0 mmol) and reacted with dichloromethylphosphine (4.1 ml, 0.46 mmol) according to General Method I. The residue was purified by fractional distillation (bp=110° C.@2.8 mm Hg) affording 5.9 g (68%) of bis(3-methoxypropyl)methylphosphine as a mobile colorless oil. $^{31}$PNMR(Benzene-d$_6$):δ −43.3. MS (HREI) m/z=192.1279 (192.1279 calc'd for C$_9$H$_{21}$O$_2$P).

EXAMPLE 23

Two step synthesis of trans-[1,2-bis[dihydro-2,2,5,5-tetramethyl-3(2H)furanone-4-methyleneamino]ethane]-bis-[tris(3-methoxypropyl)phosphine]technetium-99 m(III)

18 mg of 1,2-bis[dihydro-2,2,5,5-tetramethyl(2H)furanone-4-methyleneamino]ethane was dissolved in 0.1 mL of ethanol. A solution of 0.1 mL of $^{99m}$TcO$_4$- in saline (obtained from a molybdenum generator), diluted with 0.9 mL of water, was added and the mixture was deareated for 15 min with argon. A solution of 30 microliters of 1M KOH and 15 microgams of stannous chloride (in 5 microliters of ethanol) were added. The mixture was heated for 15 min. at 70° C. and cooled to room temperature. The reaction was monitored by HPLC on a PRP-1, 250×4.1 mm, 10 micron column in 80:20 MeOH:H$_2$O (50 mM NH$_4$OAc) at a flow rate of 1.5 mL/min. A volume of 300 microliters of a solution of 225 mg of tris(3-methoxypropyl)phosphine and 0.9 mL of 1M HCl in 9.1 mL of ethanol was added and the solution was heated for 10 min. at 70° C. and cooled to room temperature. The reaction mixture was purified by HPLC on a PRP-1, 250×4.1 mm, 10 micron column in 80:20 MeOH:H$_2$O (50 mM NH$_4$OAc) at a flow rate of 1.5 mL/min. The HPLC eluate (0.9 mL) was diluted to 8.0 mL with the addition of 7.1 mL of 0.9% sodium chloride to give a solution of trans-[1,2-bis[dihydro-2,2,5,5-tetramethyl-3(2H)furanone-4-methyleneamino]ethane]bis[tris(3-methoxypropyl)-phosphine]technetium-99 m(III) ready for use. The radiochemical purity was 90% as determined by HPLC on a PRP-1, 150×4.1 mm, 10 micron column in 45:55 CH$_3$CN:0.1M NH$_4$OAc at a flow rate of 2.0 mL/min; tr=5.7 min.

EXAMPLE 24

Two step synthesis of trans-[1,2-bis[dihydro-2,2,5,5-tetramethyl-3(2H)furanthione-4-methyleneamino]ethane]-bis[tris(3-methoxypropyl)phosphine]technetium-99m (III)

10 mg of 1,2-bis[dihydro-2,2,5,5-tetramethyl-3(2H)-furanthione-4-methyleneamino]ethane was dissolved in 0.1 mL of ethanol. A solution of 0.2 mL of $^{99m}$TcO$_4$- in saline (obtained from a molybdenum generator), diluted with 0.8 mL of water, was added and the mixture was deareated for 15 min. with argon. A solution of 30 microliters of 1M KOH and 15 micrograms of stannous chloride (in 5 microliters of ethanol) were added. The mixture was heated for 15 min. at 70° C. and cooled to room temperature. The reaction was monitored by HPLC on a PRP-1, 250×4. 1 mm, 10 micron column in 80:20 MeOH:H$_2$O (50 mM NH$_4$OAc) at a flow rate of 1.5 mL/min. A volume of 300 microliters of a solution of 225 mg of tris(3-methoxypropyl)phosphine and 0.9 mL of 1M HCl in 9.1 mL of ethanol was added and the solution was heated for 10 min. at 70° C. and cooled to room temperature. The reaction mixture was purified by HPLC on a PRP-1, 250×4.1 mm, 10 micron column in 80:20 MeOH:H$_2$O (50 mM NH$_4$OAc) at a flow rate of 1.5 mL/min. The HPLC eluate (0.9 mL) was diluted to 8.0 mL with the addition of 7.1 mL of 0.9% sodium chloride to give a solution of trans-[1,2-bis-[dihydro-2,2,5,5-tetramethyl-3(2H)furanthione-4-methyleneamino]ethane]bis [tris(3-methoxypropyl)-phosphine]technetium-99 m(III) ready for use. The radiochemical purity was 99% as determined by HPLC on a PRP-1, 150×4.1 mm, 10 micron column in 45:55 CH$_3$CN:0.1M NH$_4$OAc at a flow rate of 2.0 mL/min; tr=8.6 min.

EXAMPLE 25

Two step synthesis of trans-[1,2-bis[dihydro-2,2,5,5-tetramethyl-3(2H)furanone-4-methyleneamino]ethane]bis-tris(2-(2-(1,3-dioxanyl))]ethylphosphine]technetium-99m(III)

18 mg of 1,2-bis[dihydro-2,2,5,5-tetramethyl-(3(2H)furanone-4-methyleneamino]ethane was dissolved in 0.1 mL of ethanol. A solution of 0. 1 mL of $^{99m}$TcO$_4$- in saline (obtained from a molybdenum generator), diluted with 0.9 mL of water, was added and the mixture was deareated for 15 min. with argon. A solution of 30 microliters of 1M KOH and 15 micrograms of stannous chloride (in 5 microliters of ethanol) were added. The mixture was heated for 15 min. at 70° C. and cooled to room temperature. The reaction was monirored by HPLC on a PRP-1, 250×4.1 mm, 10 micron column in 80:20 MeOH:H$_2$O (50 mM NH$_4$OAc) at a flow rate of 1.5 mL/min. A volume of 150 microliters of a solution of 60 mg of tris(2-(2-(1,3-dioxanyl))]ethylphosphine and 20 microliters of 12M HCl in 2 mL of ethanol was added and the solution was heated for 15 min. at 70° C. and cooled to room temperature. The reaction mixture was purified by HPLC on a PRP-1,250×4.1 mm, 10 micron column in 80:20 MeOH:H$_2$O (50 mM NH$_4$OAc)-95:5 MeOH:H$_2$O (50 mM NH$_4$OAc) at a flow rate of 1.5 mL/min. The HPLC eluate (0.4 mL) was diluted to 6.0 mL with the addition of 5.4 mL of 0.9% sodium chloride to give a solution of trans-[1,2-bis-[dihydro-2,2,5,5-tetramethyl-3(2H)furanone-4-methyleneamino]ethane]bis[tris(2-(2-(1,3-dioxanyl)-)]ethyl-phosphine]technetium-99 m(III) ready for use. The radiochemical purity was 99% as determined by HPLC on a PRP-1, 150×4.1 mm, 10 micron column in 45:55 CH$_3$CN:0.1M NH$_4$OAc at a flow rate of 2.0 mL/min; tr=8.6 min.

EXAMPLES 26–37

The compounds listed below were synthesized using the procedures substantially in accordance with those of Examples 23–25:

trans-[1-[dihydro-2,2,5,5-tetramethyl-3(2H)furanthione-4-methyleneamino]-2-[dihydro-2,2,5,5-tetramethyl-3(2H)-furanone-4-methyleneamino]ethane]bis[tris(3-methoxypropyl)phosphine]technetium-99 m(III), trans-[1,2-bis[dihydro-2,2,5,5-tetramethyl-3(2H)-furanthione-4-methyleneamino]ethane]bis[tris(2-(2-(1,3dioxanyl))]ethylphosphine]technetium-99 m(III), trans-[1,2-bis[dihydro-2,2,5,5-tetramethyl-3(2H)furanone-4-methyleneamino]ethane]bis[bis(3-methoxypropyl)methylphosphine]technetium-99 m(III), trans-[1,2-bis[dihydro-2,2-dimethyl-3(2H)furanone-4-methyleneamino]ethane]bis[tris(3-methoxypropyl)phosphine]-technetium-99 m(III), trans-[1,2-bis[dihydro-2,2-dimethyl-3(2H)furanone-4-methyleneamino]ethane]bis[tris(4-methoxybutyl)-phosphine]-technetium-99 m(III), trans-[1,2-bis[dihydro-2,2,5,5-tetramethyl-3(2H)furanone-4-methyleneamino]ethane]bis[(3-methoxypropyl)dimethylphosphine]technetium-99 m(III), trans-[1,2-bis[dihydro-2,2,5,5-tetramethyl-3(2H)furanone-4-methyleneamino]ethane]bis[trimethylphosphine]-technetium-99 m(III), trans-[1,2-bis[dihydro-2,2,5,5-tetramethyl-3(2H)furanone-4-methyleneamino]ethane]bis[bis(3-methoxypropyl)phosphine]technetium-99 m(III), trans-[1,2-bis[dihydro-2,2-dimethyl-3(2H)furanthione-4 methyleneamino]ethane]bis[tris(3-methoxypropyl)phosphine]technetium-99 m(III), trans-[1-[dihydro-2,2,5,5-tetramethyl-3(2H)furanthione-4-methyleneamino]-2-[dihydro-2,2,5,5-tetramethyl-3(2H)furanone-4-methyleneamino]ethane]bis[bis(3-methoxypropyl)methylphosphine]-technetium-99 m(III), trans-[1-[dihydro-2,2,5,5-tetramethyl-3(2H)furanthione-4-methyleneamino]-2-[dihydro-2,2,5,5-tetramethyl-3(2H)-furanone-4-methyleneamino]e- thane]bis[(3-methoxypropyl)dimethylphosphine]-technetium-99 m(III), and trans-[1-[dihydro-2,2,5,5-tetramethyl-3(2H)furanthione-4-methyleneamino]-2-[dihydro-2,2,5,5-tetramethyl-3(2H)furanone-4-methyleneamino]ethane]bis[tris(2-(2-(1,3-dioxanyl))]ethylphosphine]-technetium-99 m(III).

EXAMPLE 38

One step synthesis of trans-[1-[dihydro-2,2,5,5-tetramethyl-3(2H)furanthione-4-methyleneamino]-2-[dihydro-2,2,5,5-tetramethyl-3(2H)furanone-4-methyleneaminoethane]bis[tris(3-methoxypropyl)phosphine]technetium99 m(III)

2 mg of 1-[dihydro-2,2,5,5-tetramethyl-3(2H)furanthione-4-methyleneamino]-2-[dihydro-2,2,5,5-tetramethyl3(2H)furanone-4-methyleneamino]ethane was dissolved in 0.1 mL of ethanol, diluted with 1 mL of water and the mixture was deareated for 15 min. with argon. 0.05 mL of 0.1M KOH and 0.008 mL of stannous chloride solution (3 mg/mL in ethanol) were added. A volume of 0.05 mL of a solution of 0.06M tris(3-methoxypropyl)phosphine hydrochloride was added. A solution of 0.1 mL of $^{99m}TcO_4$ in saline (obtained from a molybdenum generator) was added. The mixture was heated for 15 min. at 100° C. and cooled to room temperature to give a solution of trans-[1-[dihydro-2,2,5,5-tetramethyl-3(2H)-furanthione-4-methyleneamino]-2-[dihydro-2,2,5,5-tetra-methyl-3(2H)furanone-4-methyleneamino]ethane]bis[tris(3-methoxypropyl)-phosphine]technetium-99 m(III). The radiochemical purity was 97% as determined by HPLC on a PRP-1, 250×4.1 mm, 10 micron column in 45:55 $CH_3CN$:0.1M $NH_4OAc$ at a flow rate of 2.0 mL/min; tr=8.7 min.

The myocardial imaging agents of the present invention specified above may be used in any pharmaceutically acceptable imaging vehicle. These include those suitable for injection, such as aqueous buffer solutions, e.g. (Tris hydroxymethyl) aminomethane and its salt, phosphate, citrate, bicarbonate, e.g., sterile water for injection, physiological saline, and balance ionic solutions containing chloride and/or bicarbonate salt of normal blood plasma cations such as calcium, sodium, potassium, and magnesium. Other buffer solutions are described in Remington's Practice of Pharmacy, 11th Edition, for example on page 170.

Additionally, the pharmaceutically acceptable vehicle may contain stabilizers, antioxidants and other adjuncts. Stabilizers include gelatin or other materials in stabilizing amounts to prevent aggregation of the particles, antioxidants, and antioxidants amounts of such as reducing sugars, (e.g. fructose, or free acid, or metal salts of gentisic acid (ascorbic acid and other adjutants such as reducing agents, preferably stanis salts, intermediate exchange ligands, and exchange amounts, such as metal salts of tartrate, glutinate or citrate, as well as bulking agents and bulking amounts, such as lactose).

The myocardial imaging agents may also be formulated in a one step procedure as a lyophilized kit wherein the radioisotope solution is injected for reconstitution or is an autoclaved or radiation sterilized solution which is then treated with the radioisotope. The product may be formulated in a two-step scheme as described above where the radioisotope is bound to the equatorial ligand and then is complexed with or without purification with the axial ligand. The steps just described may additionally require heating and the intermediates or final products may require purification before use.

The concentration of the myocardial imaging agent in a pharmaceutically acceptable vehicle varies with its particular use. A sufficient amount is present to provide satisfactory imaging. This amount will vary with the physical properties of the imaging agent being used.

The myocardial imaging agent composition is administered in a radioactive dose of from 0.01 mCi/mL to 10 mCi/mL most preferably 2 mCi/mL to 5 mCi/mL. The administration dose per human is usually in the range of 10 to 30 mCi/mL.

The method of imaging of the heart can be carried out by known scanning techniques after waiting an appropriate period of time to permit blood clearance of the radio-pharmaceutical. For example, time dependent scintiscans of the chest region of a patient can be used. A computer interfaced 16 crystal, Ohio Nuclear Spectrometer can be used for these scans. The complexes of the present invention can also be used in a single photon emission computed tomography as described in Beyer, et al. *Diagnostic Nuclear Medicine.* Vol. I, No. 2, page 10 (Summer of 1984). Other metal radioisotopes found to be particularly useful in PET (positron emission tomography) when used as the radioisotope in the present invention are $Cu^{2+}$ and $Ga^{3+}$.

The present invention is also particularly suitable for use in a kit preparation. The kit preparation would consist of either one or two sterile, pyrogen free vials. In the "Two-Vial Kit" the first vial contains an effective equatorial ligand having the structure shown in Formula 3 or 4 above in combination with an effective reducing agent, in this case, tin chloride. This would be a lyophilized composition. The second vial would contain a protective salt of the phosphine ligand, such as those described above. Typically, this would be the phosphine salt bonded to HCL, $H_2SO_4$, iron (II), copper (I), or zinc (II). The acid salts are preferred. The kit would be prepared by injecting the purified 99 m-technetium obtained from a molybdenum generator into the first vial. Saline is added to the second vial to dissolve the protected ligand. The saline solution is then added to the first vial, which is heated to affect conversion to Tc(III). The contents of the first vial can be directly injected into the patient without further purification.

The "One Vial Kit" would include an effective equatorial ligand having the structure shown in Formulas 3 and 4 above, in combination with an effective reducing agent such as tin chloride, a protective salt of the phosphine ligand such as those described above, and a bulking agent. The kit would be prepared by injecting the purified 99 m-technetium obtained from a molybdenum generator into the vial. Saline is also added to the vial to dissolve the protected ligand. The vial is then heated to affect conversion to Tc(III). The contents of the vial can then be directly injected into the patient without further purification.

The $^{99m}Tc(III)$ complexes of the present invention provide radio-pharmaceuticals uniquely adapted for use in the non-invasive myocardial imaging of humans. The radio-pharmaceuticals neither hang up in the blood system nor the liver while yet binding to the heart for lonq periods of time. The myocardial imaging agent of the present invention likewise shows significantly improved biodistribution and improved positive human heart images for use in diagnosis.

Accordingly, having described our invention, we claim:

1. A myocardial imaging agent comprising the following general complex formula:

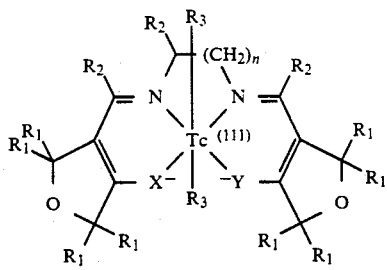

wherein the $R_1$ groups may be the same or different selected from the group consisting of hydrogen, hydroxy, $C_1-C_5$ alkyl, $C_1-C_5$ alkyl substituted by hydroxyl, ether ester, amide, ketone, aldehyde and nitrile; the $R_2$ groups may be the same or different selected from the group consisting of hydrogen, hydroxy, $C_1-C_5$ alkyl, $C_1-C_5$ alkyl substituted by hydroxyl, ether, ester, amide, ketone, aldehyde and nitrile; the X and Y groups may be the same or different selected from the group consisting of oxygen and sulfur; the $R_3$ groups may be the same or different phosphine ligands comprising the following general formula:

wherein $R_4$ is selected from the group consisting of hydrogen, $C_1-C_5$ alkyl, ether, $C_1-C_5$ alkylaryl, and $C_1-C_5$ dioxanylalkyl; and the $R_5$ groups may be the same or different from the $R_4$ group selected from the group consisting of $C_1-C_5$ alkyl, ether, $C_1-C_5$ alkylaryl, and $C_1-C_5$ dioxanylalkyl; and n is equal to 1 or 2.

2. The method of imaging the heart of a human comprising: applying intravenously an effective amount of themyocardial imaging agent claimed in claim 1 into said human and detecting radiation emitted from said complex which localizes in the heart of said human.

3. The myocardial imaging agent claimed in claim 1 wherein X and Y represent oxygen and $R_1$ represents methyl; and $R_2$ represents hydrogen.

4. The mhyocardial imaging agent claimed in claim 1 wherein X and Y represent sulfur and $R_1$ represents methyl and $R_2$ represents hydrogen.

5. The myocardial imaging agent claimed in claim 1 wherein X represents sulfur and Y represents oxygen and $R_1$ represents methyl and $R_2$ represents hydrogen.

6. The complex claimed in claim 1 wherein the $R_3$ groups are both tris(3-methoxypropyl) phosphine.

7. The complex claimed in claim 1 wherein the $R_3$ groups are both tris{2-[2-(1,3-dioxanyl)]} ethylphosphine.

8. The myocardial agent claimed in claim 1 wherein X and Y represent sulfur; $R_1$ repsresents methyl; $R_2$ represents hydrogen; $R_3$ is a phosphine ligand wherein $R_4$ and the $R_5$ groups represent ether groups, and n is equal to 1.

9. The myocardial imaging agent claimed in claim 8 wherein $R_3$ is tris(3-methoxypropyl)phosphine.

10. The myocardial imaging agent claimed in claim 8 wherein $R_3$ is tris{2-[2-(1,3-dioxanyl)]}ethylphosphine.

11. The myocardial agent claimed in claim 1 wherein X represetns oxygen and Y represents sulfur; $R_1$ represents methyl; $R_2$ represents hydrogen; $R_3$ is a phosphine ligand wherein $R_4$ and the $R_5$ groups represent ether groups, and n is equal to 1.

12. The myocardial imaging agent claimed in claim 11 wherein $R_3$ is tris(3-methoxypropyl)phosphine.

13. The myocardial imaging agent claimed in claim 11 wherein $R_3$ is tris{2-[2-(1,3-dioxanyl)]}ethylphosphine.

14. The myocardial imaging agent claimed in claim 1 wherein X and Y represent oxygen; $R_1$ represents methyl; $R_2$ represents hydrogen; $R_3$is a phosphine ligand wherein $R_4$ and the $R_5$ groups represent ether groups, and n is equal to 1.

15. The method of imaging the heart of a human comprising: applying intravenously an effective amount of the complex claimed in claim 14 into said human and detecting radiation emitted from said comlex which localizes in the heart of said human.

16. The myocardial imaging agent claimed in claim 14 wherein $R_3$ is tris(3-methoxypropyl)phosphine.

17. The method of imaging the heart of a human comprising: applying intravenously an effective amount of the complex claimed in claim 16 into said human and detecting radiation emitted from said complex which localizes in the heart of said human.

18. The myocardial imaging agent claimed in claim 14 wherein Rhd 3 is tris{2-[2-(1,3-dioxanyl)]}ethylphosphine.

19. The method of imaging the heart of a human comprising: applying intraveneously an effective amount of the complex claimed in claim 18 into said human and detecting radiation emitted from said complex which localizes in the heart of said human.

* * * * *